United States Patent
Wandke et al.

(10) Patent No.: US 11,102,876 B2
(45) Date of Patent: Aug. 24, 2021

(54) PLASMA TREATMENT DEVICE

(71) Applicant: CINOGY GMBH, Duderstadt (DE)

(72) Inventors: Dirk Wandke, Heilbad Heiligenstadt (DE); Mirko Hahnl, Berlingerode (DE); Karl-Otto Storck, Duderstadt (DE); Leonhard Trutwig, Duderstadt (DE); Melanie Ricke, Katlenburg-Lindau (DE)

(73) Assignee: Cinogy GmbH, Duderstadt (DE)

( * ) Notice: Subject to any disclaimer, the term of this patent is extended or adjusted under 35 U.S.C. 154(b) by 0 days.

(21) Appl. No.: 16/631,689

(22) PCT Filed: Jul. 5, 2018

(86) PCT No.: PCT/DE2018/100619
§ 371 (c)(1),
(2) Date: Jan. 16, 2020

(87) PCT Pub. No.: WO2019/015717
PCT Pub. Date: Jan. 24, 2019

(65) Prior Publication Data
US 2020/0170098 A1 May 28, 2020

(30) Foreign Application Priority Data
Jul. 19, 2017 (DE) .................. 10 2017 116 305.0

(51) Int. Cl.
*H05H 1/24* (2006.01)
*H05H 1/34* (2006.01)

(52) U.S. Cl.
CPC ............ *H05H 1/2406* (2013.01); *H05H 1/34* (2013.01); *H05H 2001/2412* (2013.01); *H05H 2245/1225* (2013.01); *H05H 2277/10* (2013.01)

(58) Field of Classification Search
None
See application file for complete search history.

(56) References Cited

U.S. PATENT DOCUMENTS

| 7,195,670 B2 * | 3/2007 | Hansen ............ B01L 3/502738 117/68 |
| 9,452,285 B2 * | 9/2016 | Draghia-Akli ....... A61N 1/0412 |

(Continued)

FOREIGN PATENT DOCUMENTS

| DE | 40 40 911 A1 | 6/1991 |
| DE | 20 2008 008 733 U1 | 12/2009 |

(Continued)

*Primary Examiner* — Amy Cohen Johnson
*Assistant Examiner* — Srinivas Sathiraju
(74) *Attorney, Agent, or Firm* — W & C IP

(57) ABSTRACT

The invention relates to a plasma treatment device for carrying out a dielectric barrier plasma discharge, comprising an electrode unit (1), which has a treatment side (5), and comprising a supply unit (10), to which the electrode unit (1) can be mechanically connected and by means of which the electrode unit can be brought into electrical contact in order to be supplied with a supply voltage necessary for the plasma generation, wherein the electrode unit (1) has an electrode arrangement, which is shielded by means of a planar dielectric (2) at least toward the treatment side (5), enables the use of different electrode units (1) with the same supply unit (10) in that the electrode unit (1) has a coding and the supply unit (10) has an identifying device for the coding and the identifying device is connected to a control device, which controls the supply voltage for the plasma generation in accordance with the identified coding.

8 Claims, 12 Drawing Sheets

(56) References Cited

U.S. PATENT DOCUMENTS

| | | | | |
|---|---|---|---|---|
| 2002/0049374 A1* | 4/2002 | Abreu | A61F 9/0017 | |
| | | | | 600/405 |
| 2002/0049389 A1* | 4/2002 | Abreu | A61B 5/412 | |
| | | | | 600/558 |
| 2008/0091135 A1* | 4/2008 | Draghia-Akli | A61N 1/0412 | |
| | | | | 604/20 |
| 2012/0232540 A1* | 9/2012 | Baur | A61B 17/00 | |
| | | | | 606/10 |
| 2014/0308930 A1* | 10/2014 | Tran | H04W 4/18 | |
| | | | | 455/414.1 |
| 2016/0236002 A1* | 8/2016 | Dirk | A61N 1/0468 | |
| 2016/0287310 A1* | 10/2016 | Nettesheim | H05H 1/24 | |
| 2017/0094769 A1* | 3/2017 | Eckert | H05H 1/2406 | |
| 2017/0231680 A1* | 8/2017 | Mahrenholz | A61N 1/44 | |
| | | | | 606/34 |
| 2018/0178024 A1* | 6/2018 | Hahnl | H05H 1/46 | |
| 2018/0221517 A1* | 8/2018 | Trutwig | H01J 37/32348 | |
| 2019/0327823 A1* | 10/2019 | Hahnl | A61L 2/14 | |
| 2020/0029414 A1* | 1/2020 | Trutwig | H05H 1/2406 | |
| 2020/0170098 A1* | 5/2020 | Wandke | H05H 1/34 | |
| 2020/0187341 A1* | 6/2020 | Wandke | A61N 1/44 | |

FOREIGN PATENT DOCUMENTS

| | | |
|---|---|---|
| DE | 10 2011 051 754 A1 | 1/2013 |
| DE | 10 2012 025 079 A1 | 3/2014 |
| DE | 10 2013 019 057 A1 | 5/2015 |
| DE | 10 2014 013 716 A1 | 3/2016 |
| DE | 10 2014 220 488 A1 | 4/2016 |
| DE | 10 2015 111 401 B3 | 9/2016 |
| GB | 2239803 A | 7/1991 |
| JP | H08 63539 A | 3/1996 |
| WO | 2016/186501 A2 | 11/2016 |

* cited by examiner

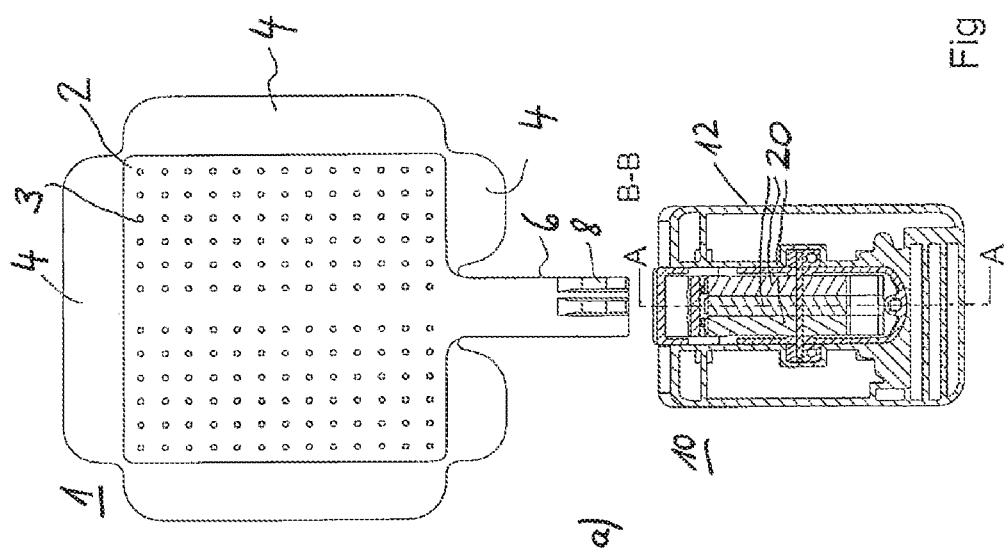

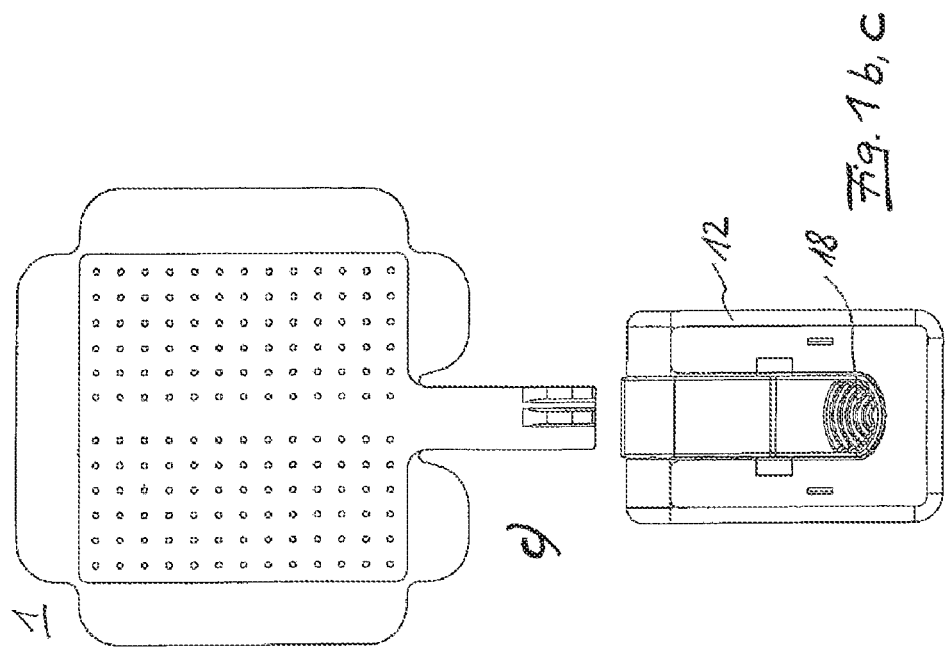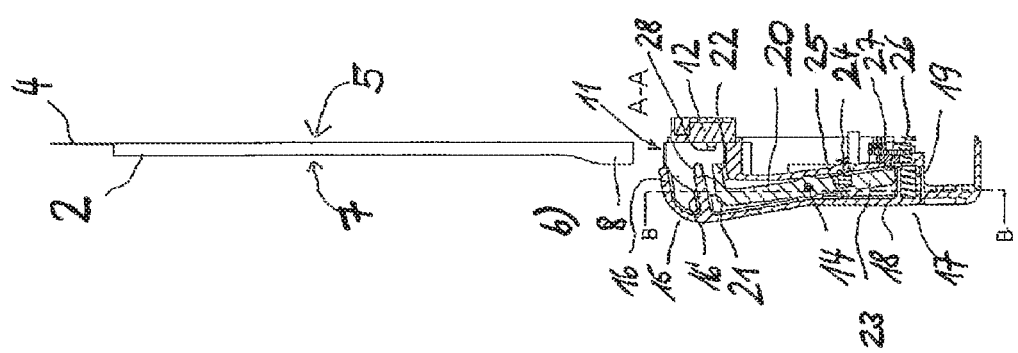

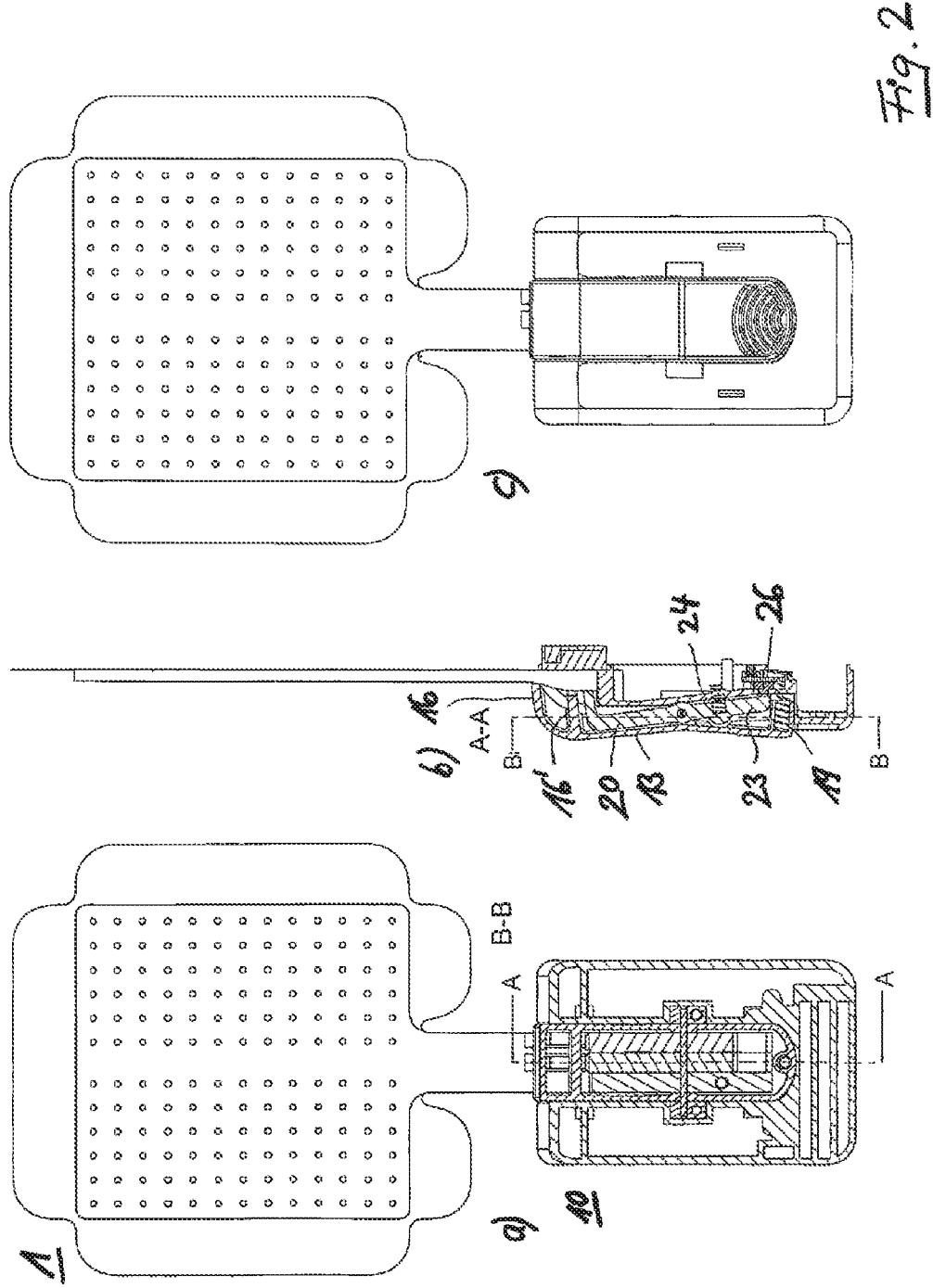

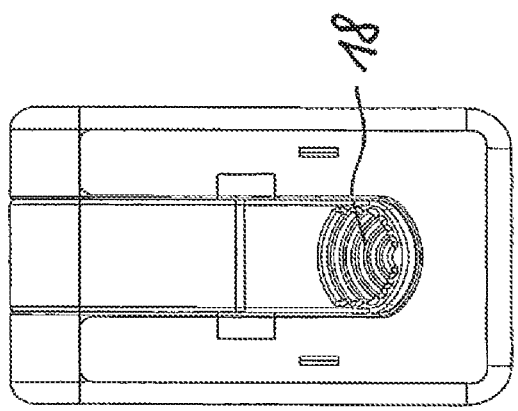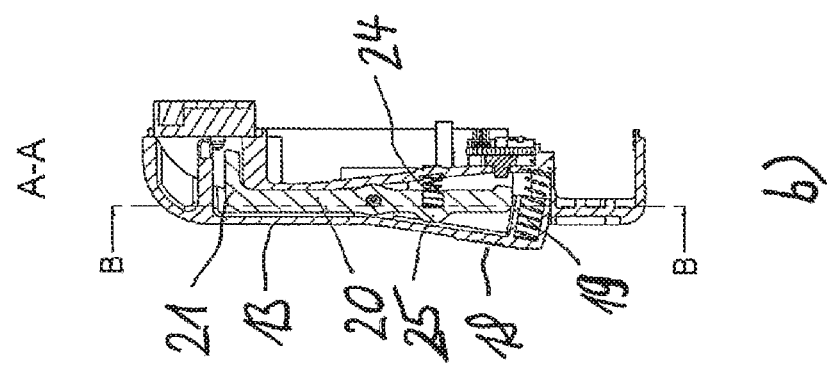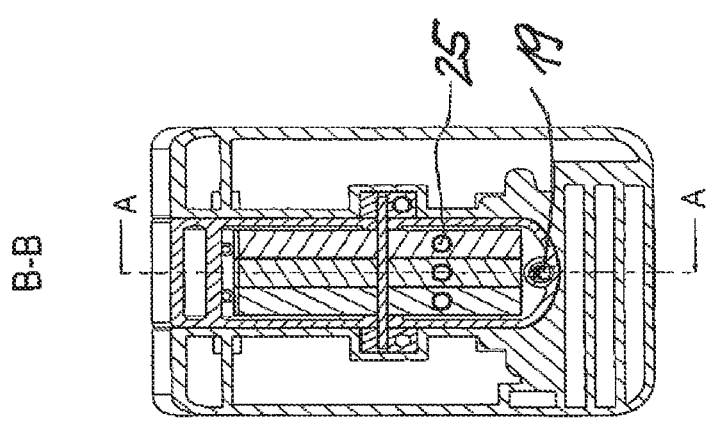

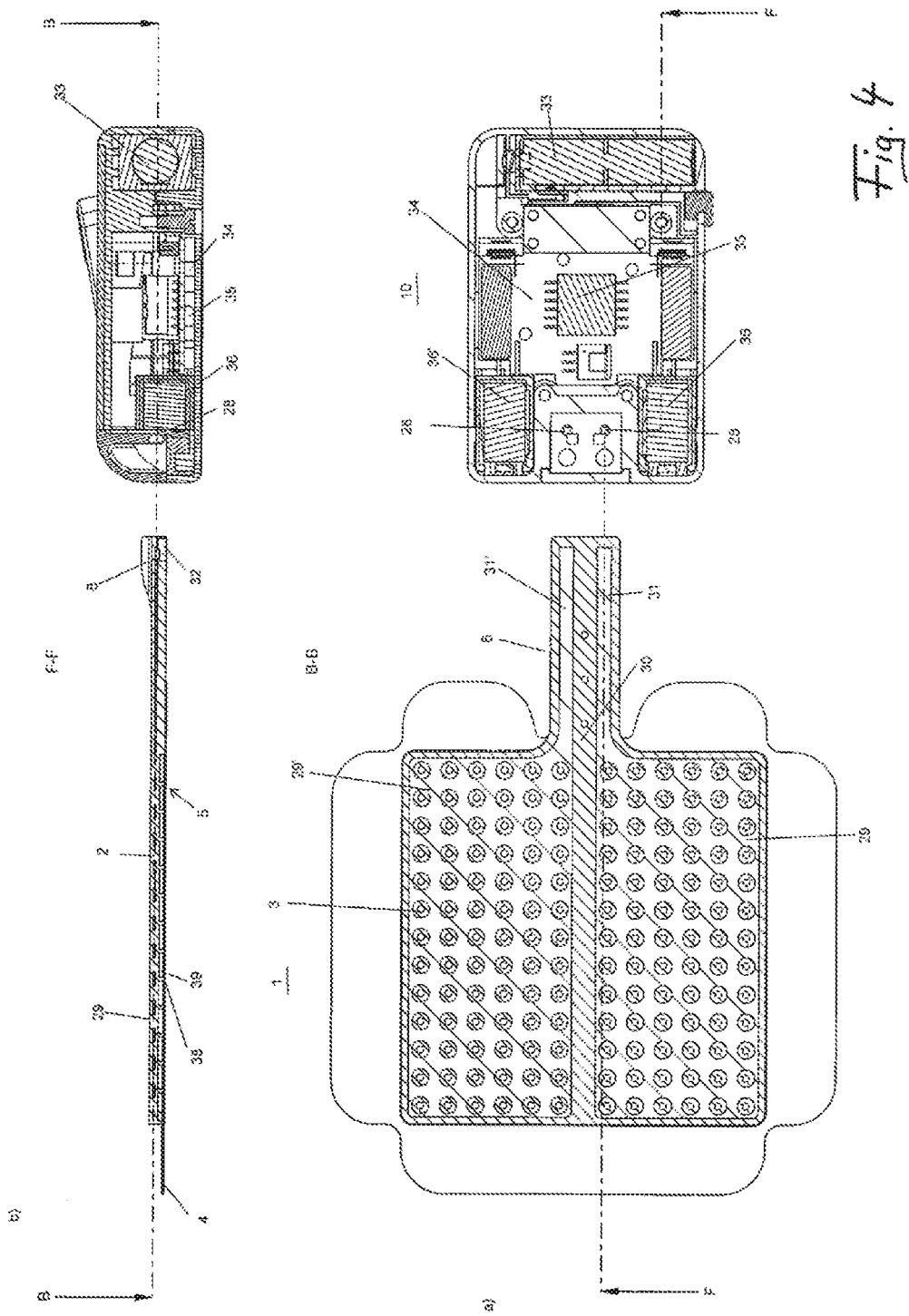

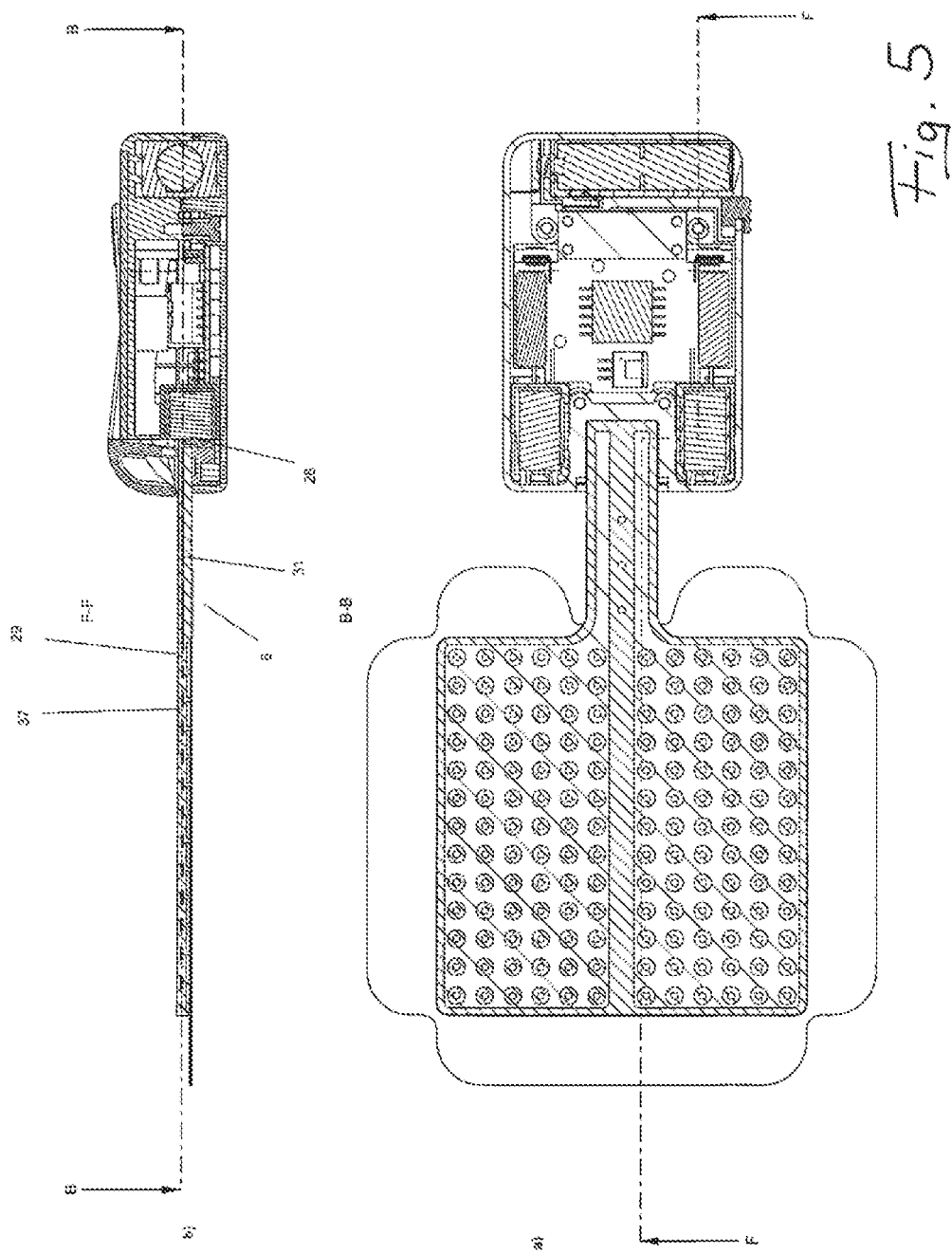

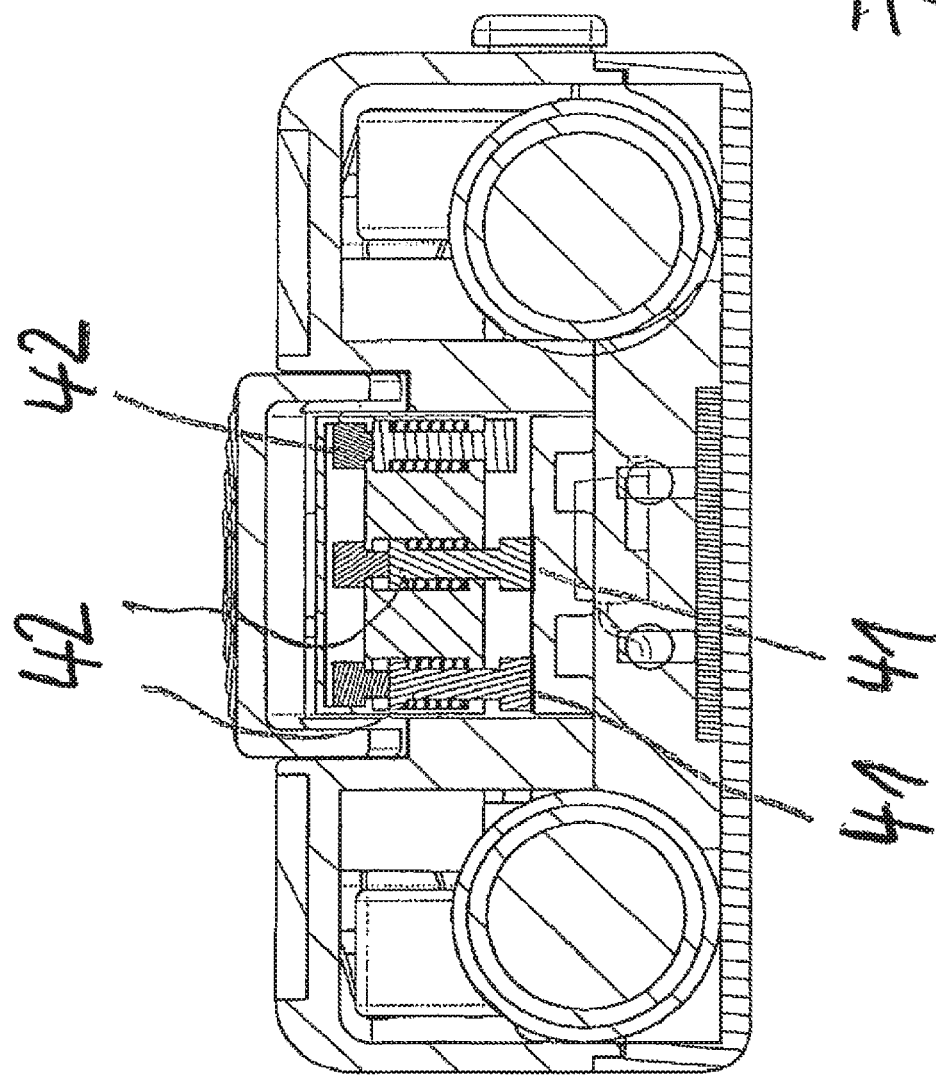

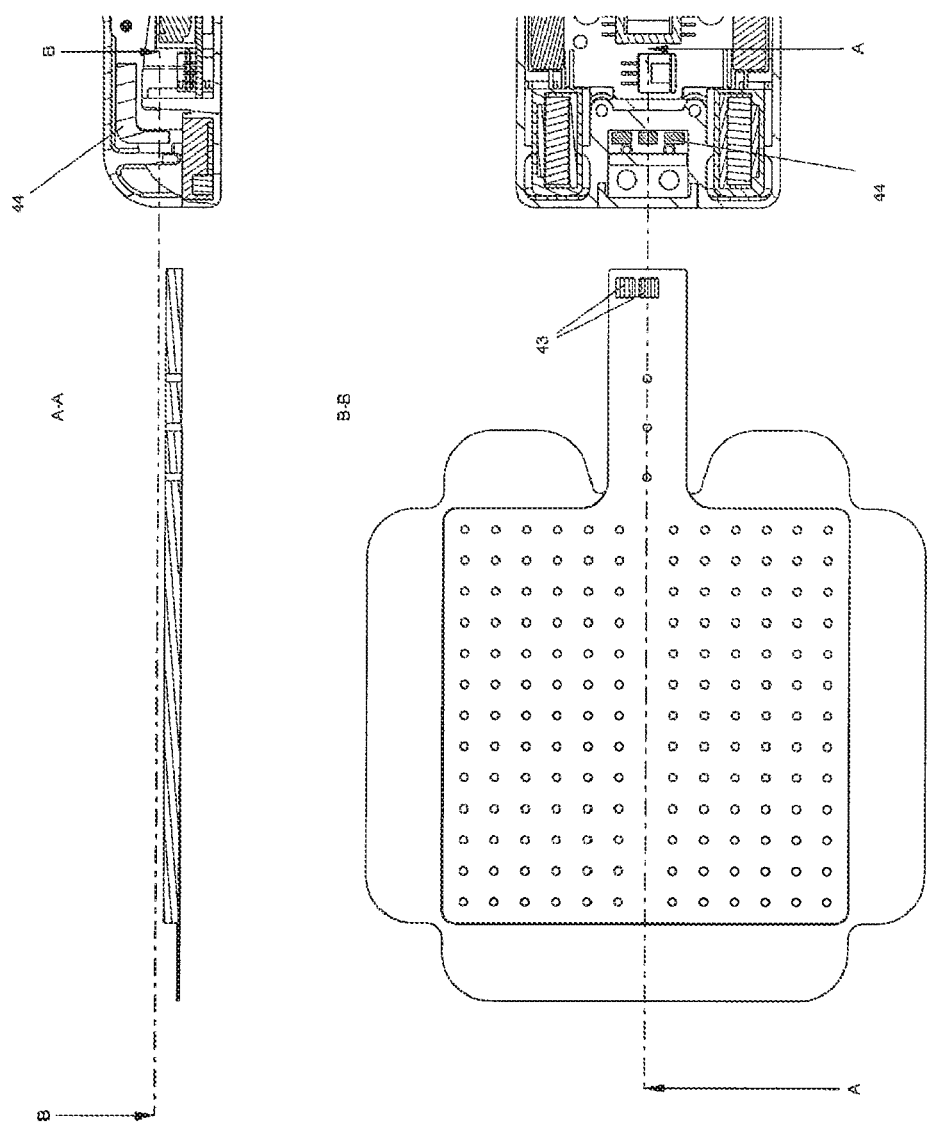

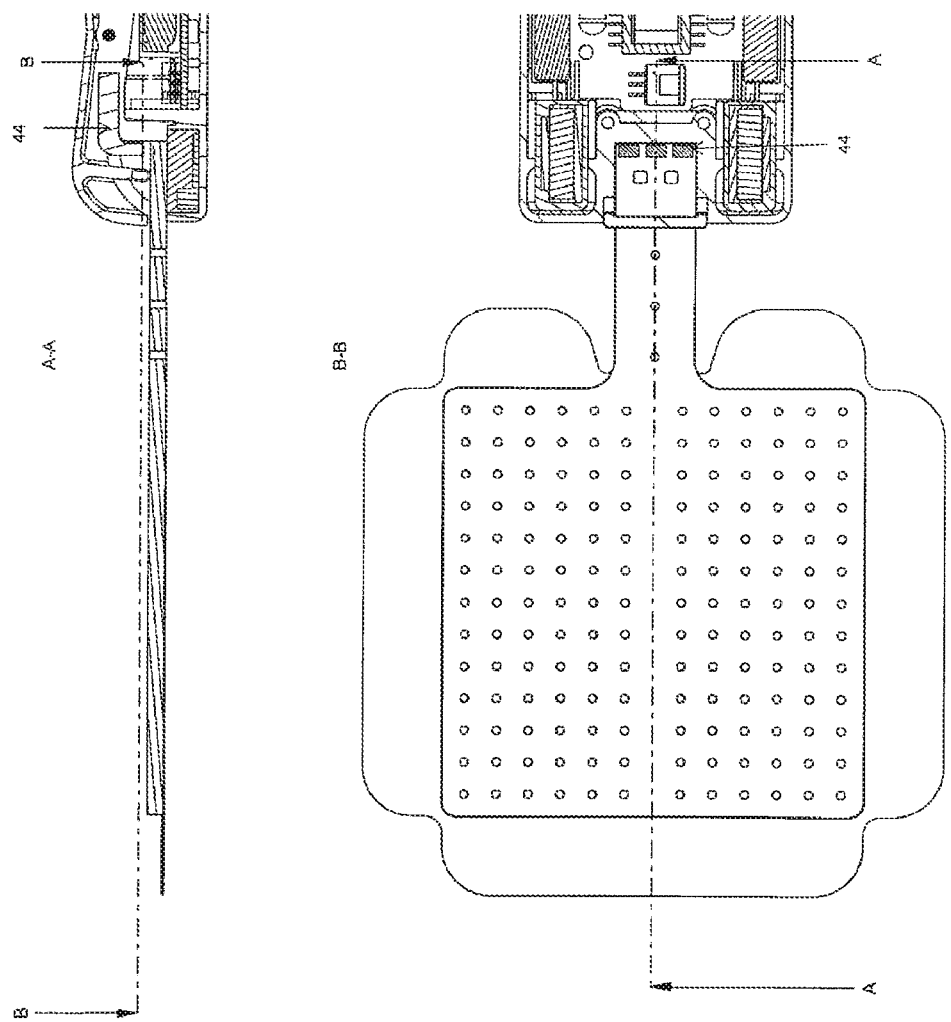

PLASMA TREATMENT DEVICE

FIELD OF THE INVENTION

The invention relates to a plasma treatment device for carrying out a dielectric barrier plasma treatment of a surface, having an electrode unit comprising a treatment side and having a supply unit, with which the electrode unit can be mechanically connected and electrically contacted in order to be supplied with a supply voltage required for the treatment, the electrode unit comprising an electrode arrangement which is shielded by a flat dielectric at least on the treatment side.

BACKGROUND

Such a plasma treatment device is known from DE 10 2014 013 716 A1. The electrode unit is in this case configured as a flat unit having a flat electrode arrangement and a flat dielectric. The materials may in this case be selected in such a way that the electrode unit, which can be placed on a wound surface or skin surface, can adapt flexibly to the surface. The electrode unit is in this case provided with an appendage into which both the electrode arrangement and the dielectric extend. The appendage of the electrode unit can be inserted into a recess of a supply unit and can be mechanically held there by a lever clamping mechanism. In this case, the electrode arrangement is likewise electrically contacted with the supply unit. The supply unit in this case contains a high-voltage stage which generates the high voltage required for the dielectric barrier plasma treatment, generally in the form of alternating high-voltage pulse trains, from a supplied mains voltage.

In the known treatment device, the electrode unit is replaceably connected to the supply unit because the electrode unit is intended for single use. This has the advantage that the electrode units can be produced and packaged in a sterile fashion, and sterilization measures are not required before or after use of the electrode unit.

SUMMARY

The object of the present invention is to configure a plasma treatment device of the previously known type in such a way that it can be used for a wider field of application and is simple to handle.

In order to achieve this object, a plasma treatment device of the type mentioned in the introduction is characterized in that the electrode unit comprises encoding and the supply unit comprises a recognition instrument for the encoding, and the recognition instrument is connected to a control instrument which controls the supply voltage as a function of the recognized encoding.

The present invention is based on the concept that the replaceability of the electrode unit, achieved by the releasable connection between the supply unit and the electrode unit, makes it possible in principle to use the same supply unit with different electrode units. For wound care, in particular, electrode units of different sizes may be used in order to treat wound surfaces of different sizes with the dielectric plasma discharge, and thereby reduce the germs in the wound area and promote healing by stimulating the microcirculation in the wound region. When electrode units of different sizes are connected to the supply unit, however, the problem arises that the supply unit produces voltage pulses with constant energy contents even though electrode units of different sizes require levels of energy delivery of different sizes. By the encoding according to the invention of the electrode unit, it is now possible to connect electrode units of different sizes to the supply unit and to supply the electrode unit with the amount of energy suitable for its size.

In the same way, by virtue of the encoding of the electrode unit, it is possible to adapt the voltage delivered from the supply unit to the electrode unit when one electrode unit is intended and designed for wound care but another electrode unit is intended and designed for a cosmetic treatment of the skin surface. In this way, suitable treatment programs may be provided by the supply unit for the respective electrode unit. It is therefore possible to carry out the encoding according to the invention not only for different electrode sizes but also for differently designed electrodes which are adapted for particular applications, for example by different configurations of the treatment side of the electrode unit.

Furthermore, it is possible to adapt the high voltage delivered to the electrode unit in accordance with whether skincare or healing substances are arranged on the treatment side, as is known for example from DE 10 2015 111 401 B3 or from DE 10 2013 019 057 A1. In the same way, the possible delivery of liquid or gaseous substances through insulated channels in the dielectric (cf. DE 10 2014 013 716 A1) may also be taken into account.

The encoding according to the invention may be configured in a variety of ways on the electrode unit. In one embodiment, the electrode unit comprises an appendage which can be inserted into an e.g. slot-shaped recess of the supply unit, and which carries the encoding. In this case, the mechanical connection, the electrical contacting and the transmission of the encoding may be carried out by the configuration of the appendage.

In a mechanical configuration of the encoding, it may have the form of elevations arranged next to one another, and the recognition instrument may be formed with rocker switches that can be actuated by the elevations. In this embodiment, the recognition of the encoding and the corresponding controlling of the supply voltage may be carried out by the rocker switches, if the rocker switches are configured for switching over the supply voltage in the supply unit.

As an alternative, the elevations may also be evaluated without a current supply, for example by their acting on piezo elements in the supply unit and thus converting the encoding into voltage signals.

In another embodiment, the encoding is configured in optical form and can be recognized by an optical recognition instrument in the supply unit.

This is likewise the case if the electrode unit contains a transponder for the encoding, which can be interrogated wirelessly by means of the recognition instrument of the supply unit. In order to ensure that the recognition instrument does only recognize the electrode unit which the supply unit is mechanically and electrically connected, a detector may be provided in the supply unit, which generates an interrogation signal for the recognition instrument. This ensures that the interrogation does not take place until the electrode unit is connected to the supply unit.

A further possibility for the recognition of the encoding and controlling of the consists in the encoding being carried out by means of at least one permanent magnet, by which at least one switch of the supply instrument can be actuated.

It is readily apparent that the connection of the electrode unit to the supply unit may be carried out in any way familiar to the person skilled in the art if a securely contacting electrical and a not unintentionally releasing mechanical connection is in this case established. The invention is therefore not restricted to a particular design configuration of the electrode unit and/or of the supply unit.

The supply unit may be connected to a conventional current supply by means of a cable. It is furthermore possible for the high voltage to be delivered directly to the supply unit, this voltage then merely being modified in the supply unit in accordance with the encoding. It is furthermore important that the supply unit may also be configured autonomously by its generating the required high-voltage signals from a battery voltage. The batteries are in this case expediently arranged in the supply unit itself.

DESCRIPTION OF THE DRAWINGS

The invention will be explained in more detail below with the aid of a nonrestrictive exemplary embodiment.

FIG. 1a) shows a horizontal section through one exemplary embodiment of a supply unit and a plan view of an electrode unit;

FIG. 1b) shows a vertical section along the line A-A of FIG. 1a) through the supply unit and a side view of the electrode unit;

FIG. 1c) shows a plan view of the supply unit and the electrode unit, respectively in the not yet connected state;

FIGS. 2a) to 2c) show representations according to FIGS. 1a) to 1c), but in the assembled state of the supply unit and electrode unit;

FIGS. 3a) to 3c) show the representations according to FIGS. 1a) to 1c) only for the supply unit in the inactive state;

FIGS. 4a) and 4b) show the exemplary embodiment according to FIG. 1 with a schematic representation of the electronics in the unconnected state of the supply unit and electrode unit;

FIGS. 5a) and 5b) show the representations corresponding to FIG. 4 in the connected state of the electrode unit and supply unit;

FIG. 9 shows a cross-sectional representation according to FIG. 6 for the second exemplary embodiment;

FIGS. 10a) and 10b) show a representation of a third exemplary embodiment with optical recognition in the unconnected state of the supply unit and electrode unit;

FIG. 11 shows the representations according to FIG. 10 in the connected state of the supply unit and electrode unit.

DETAILED DESCRIPTION

Figure 6:
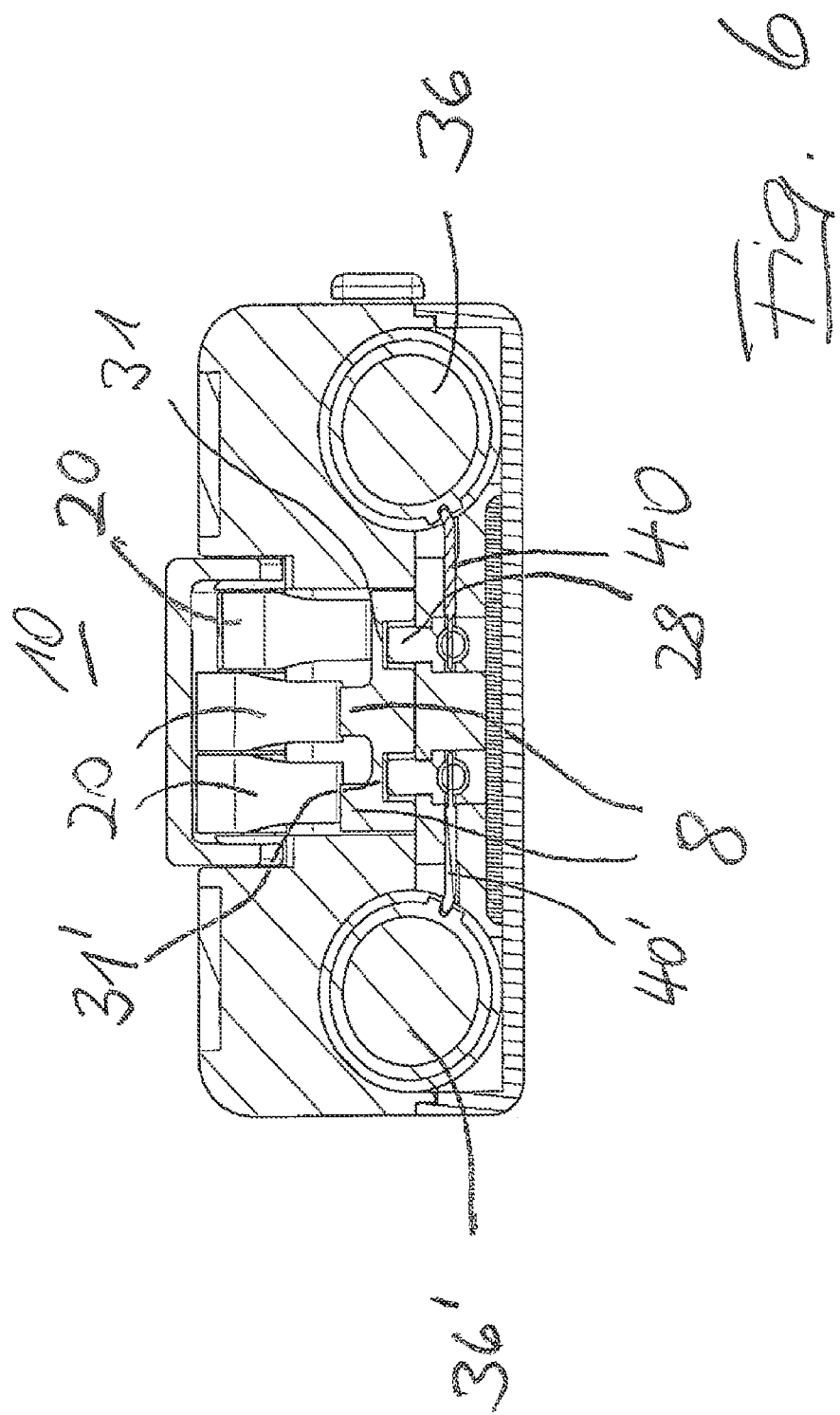
FIG. 6 shows a cross section to illustrate the rocker switch positions in the connected state of the electrode unit and supply unit.

FIGS. 1 to 3 primarily represent the mechanically design features of a first embodiment. FIG. 1 shows an electrode unit 1 which is flatly configured. The drawing only represents a dielectric 2, in which there are through-openings 3 distributed over the surface, through which wound secretion may be aspirated when the electrode unit 1 is used as a wound dressing, or in other treatment cases a gas or a liquid may be delivered onto the skin surface. The dielectric 2 comprises flexible thin appendages 4, which are configured adhesively on a treatment side 5 of the electrode unit 1, so as to fasten the electrode unit 1 on the skin of a human body in the manner of an adhesive bandage. Since only views onto the electrode unit 1 are represented and the dielectric 2 encloses an electrode arrangement on all sides, the electrode arrangement is not represented in FIGS. 1 to 3.

The electrode unit 1, i.e. the dielectric 2 with the electrode arrangement embedded therein, is flatly configured. Accordingly, the electrode unit comprises a large treatment side and a large opposite upper side 7, the dimensions of which are large in comparison with the height, i.e. the distance between the treatment side 5 and the upper side 7. Preferably, the material of the dielectric 2 and of the electrode embedded therein are flexible, so that the electrode unit 1 can be adapted to an uneven skin surface.

Both the dielectric 2 and the electrode arrangement embedded therein extend through the appendage 6. On the upper side, at the free end of the appendage 6, two bar-shaped elevations 8 are represented next to one another, which occupy approximately two thirds of the width of the appendage 6. Three such elevations 8 may therefore be arranged over the width of the appendage 6. The presence of an elevation 1 corresponds to a digital "1" and the absence of the elevation corresponds to a digital "0". With three bits, as is known, $2^3=8$ different encodings can be produced. In many cases, this number of encoding possibilities is not required, so that in particular cases it is also possible to use only two elevations (four different encodings) or only one elevation (two different encodings). Of course, the number of elevations 8 may also be increased if this seems necessary.

The dielectric 2 is preferably formed by a castable or injection-moldable plastic. The embedded electrode may be a flexible metal foil, but also a thin layer of a plastic provided with conductive additives. Preferably, the material of the dielectric 2 and of the embedded electrode are of the same type, for example both silicones.

In the exemplary embodiment represented, the elevations 8 are configured in the form of a ramp, the function of which will be explained in more detail below.

The electrode unit 1 can be connected to a supply unit 10. The connection is carried out by means of the appendage 6, for the reception of which the supply unit 10 comprises a slot-shaped recess 11 in a housing 12. The slot-shaped recess 11 can be locked or released by means of a two-armed actuation lever 13. The two-armed actuation lever 13 is rotatably mounted on a rotation axle 14 mounted in the housing 12. A front end 15 of the actuation lever is configured to be elbowed in order to lock the slot-shaped recess 11, and forms two locking bars 16, 16' arranged behind one another in the insertion direction of the appendage 6. On the other arm of the two-armed lever 13, at the rear end 17 there is a fluted pressure surface 18 by which the actuation lever 13 can be pressed with its rear end 17 into the housing against the force of a return spring 19. This pressed position is represented in FIG. 1b). In this position, the slot-shaped recess 11 is opened and makes it possible to insert the appendage 6 of the electrode unit 1.

Covered by the actuation lever, which extends substantially over the width of the rotation axle 14, three rocker levers 20, the width of which corresponds to the width of the elevations 8, are rotatably mounted on the same rotation axle 14. The rocker levers 20 are also configured as two-armed levers and comprise on their front end 21 an elbow 22 which can slide as a sensing lever on the ramp-shaped elevation 8.

The other arm of the two armed rocker lever 20, forming a rear end 23 on the far side of the rotation axle 14, is braced on the housing 12 by means of a spring 24, by which the front end 21 is prestressed in the locking direction of the slot-shaped recess 11. Via a bead 25, the rear end 23 of the rocker lever 20 bears on the lower side of the actuation lever 13, so that the rocker lever is tilted when pressing on the pressure surface 18 with the actuation lever 13.

The rear end 23 of the rocker lever 20 furthermore acts on a switch 26 assigned to it on a circuit board 27 inside the housing 12.

The slot-shaped recess 11 forms an insertion channel, on the bottom of which a contact projection, which cooperates with a corresponding counter-contact on the lower side of the appendage 6. On its lower side, the appendage 6 comprises corresponding counter-contacts which are used for the electrical contacting of the electrode unit 1 with the supply unit 10 in the inserted state. The contact projection 28 is connected (this is not represented in FIG. 1) to an electronics part of the supply unit 10.

FIG. 2 illustrates the inserted state of the electrode unit 1 into the supply unit 10. In particular, FIG. 2a) shows that the return spring 19 presses the actuation lever 13 against the appendage 6, the front locking bar 16 engaging behind the ramp-shaped elevation 8. In addition, the further locking bar 16' presses on the upper side of the elevation 8 and thus ensures the locking.

FIG. 2b) furthermore illustrates that, where elevations 8 are present, the associated rocker levers 20 are pressed at the front end against the restoring force of the spring 24, so that the rear end 23 of the rocker lever 20 actuates the associated switch 26. The three switches 26 present in this embodiment therefore convert the presence of the elevations 8 acting as encoding into corresponding electrical switching signals.

FIGS. 3a) to 3c) illustrate the inactive position of the supply unit 10, in which the return spring 19 presses the actuation lever 13 into a position fully locking the slot-shaped recess 11 and the front end of the rocker lever 20 is likewise pressed in the direction of the bottom of the slot-shaped recess 11 by the spring 24. In this case, it can be seen that, by pressing on the pressure surface 18 of the actuation lever 13, not only is the actuation lever 13 rotated, but also the three rocker levers 20 are rotated via the bead 25.

FIGS. 4 to 6 show the first exemplary embodiment with a schematic representation of the electronics. The vertical section in FIG. 4a) according to the section line F-F in FIG. 4b) and the horizontal section B-B corresponding to the section line in FIG. 4a) show that an electrode arrangement of two flat electrodes 29, 29' is formed in the electrode unit, the electrodes 29, 29' being formed mirror-symmetrically with respect to one another. The two electrodes are separated from one another by the central insulating bar 30, which is formed by the dielectric 2 and extends into the appendage 6. In the same way, the electrodes 29, 29' extend into the appendage 6 and form contact strips 31, 31' there on either side of the insulating bar 30.

FIG. 4b) shows that, at the end of the appendage 6, the material of the dielectric 2 is absent on the lower side of the appendage 6 in the region of the contact strips 31, 31' and forms groove-shaped indentations 32 in which the contact strips 31, 31' are freely accessible. The groove-shaped indentations 32 are configured in such a way that the contact projections 28 protrude into them when the electrode unit 1 is inserted into the supply unit 10. At the end of the insertion movement, the contact projection 28 contacts the associated contact strips 31, 31' so that the electrical connection between the supply unit and the electrode unit 1 is established.

The electrical part of the supply unit 4 contains batteries 33 so that the supply unit 10 operates autonomously according to this exemplary embodiment, i.e. it does not require a lead for a supply voltage. Connected to the batteries 33, there is a circuit board 34 for producing an intermediate voltage. In a controller 35, represented by an IC circuit, the DC battery voltage is chopped and converted into voltage pulses. These voltage pulses are delivered to 2 coils 36, 36' in such a way that high-voltage pulses are formed in them. Because of oscillation processes, the high-voltage pulses may contain a plurality of oscillations with decreasing amplitude. The high-voltage pulses formed by the coils 36, 36' are in antiphase, so that the sum of their instantaneous amplitudes is always zero. In this case "zero" is a reference potential, for example ground.

The antiphase high-voltage pulses reach the two contact projections 38, so that the two electrodes 29, 29' are respectively supplied with high-voltage pulses which are in antiphase with one another and of equal magnitude. With these pulses, the corresponding plasma fields are formed below the electrodes 29, 29'.

In the horizontal section according to FIG. 4a), it can also be seen that the electrodes 29, 29' likewise comprise indentations 37 around the through-openings 3 of the dielectric 2, although these are larger than the through-openings 3 so that material of the dielectric 2 bounds the through-openings 3 in the region of the through-openings 3 in the indentations 37. In this way, direct contact of a fluid with the electrodes 29, 29' is avoided. It can furthermore be seen that the dielectric 2 forms chambers 39 bounded by bars 38 on the treatment side 5 in the flat region of the electrodes 29, 29', these being open toward the treatment side and bounded horizontally by the bars 38 and on the upper side by the dielectric 2. The bars 38 may be intersecting bars of equal height, so that rectangular or square chambers 39 are formed. The chambers 39 represent structuring of the treatment side 5 of the dielectric 2, which ensures that a plasma for the treatment can be formed in air gaps on the treatment side 5 by the electrodes. The represented structuring by means of the chambers 39 is merely to be understood as exemplary, since other structuring may also be suitable, for example studs, which are directed to the surface to be treated and bear on the surface to be treated with their upper side, and between which air gaps for the plasma are formed.

FIGS. 5a) and 5b) show an electrode unit 1 and supply unit 10 in the state connected to one another. In mechanical terms, this state has already been explained with the aid of FIG. 2. FIG. 5b) shows the way in which the contact projection 28 (represented only in half-section) engages into the recess 32 (cf. FIG. 4b)) on the lower side of the appendage 6 and therefore directly contacts the contact strips 31 of the electrode 29.

Figure 7:
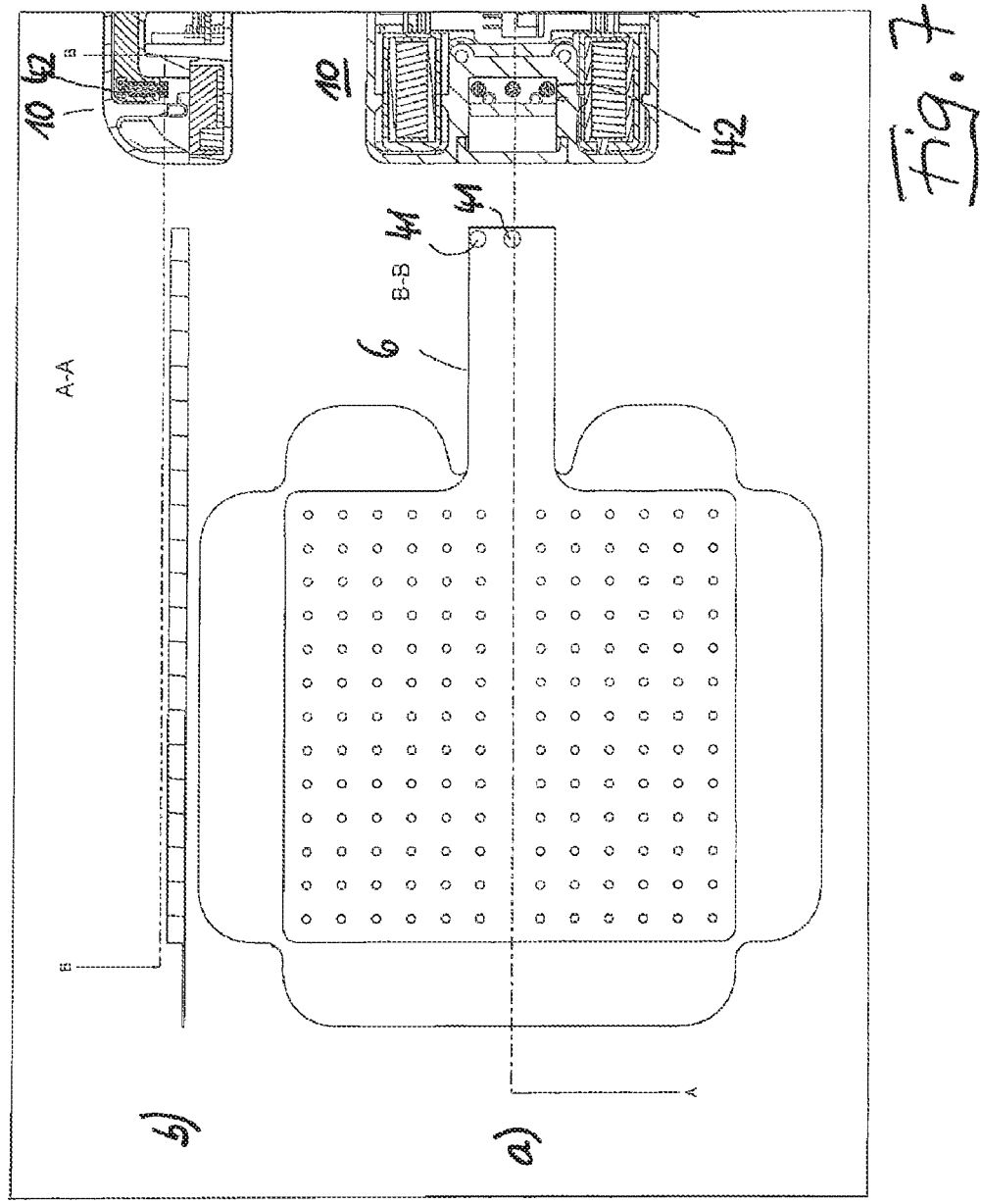
FIGS. 7a) and 7b) show sectional representations of a second exemplary embodiment with magnetic actuation of microswitches in the unconnected state of the electrode unit and supply unit.

The vertical section through the supply unit 10 in the region of the coils 36, 36' according to FIG. 6 illustrates the encoding by the elevations 8 and the rocker levers 20 actuated or not actuated by them. FIG. 6 furthermore shows a connecting line 40, 40', suitable for high voltages, between the associated coil 36, 36' and the associated contact projection 28. The contact projection 28 contacts the contact strips 31, 31' of the associated electrodes 29, 29', so that the high-voltage pulses formed in the coils 36, 36' are transmitted in antiphase to the electrodes 29, 29' The second exemplary embodiment, represented in FIGS. 7 and 8, substantially corresponds in design to the first exemplary embodiment, and differs therefrom only in that magnetic encoding is provided at the end of the appendage 6. The elevations 8 of the first exemplary embodiment are replaced with the arrangement of two small amount permanent 41, which are assigned microswitches 42 in the supply unit 10

(only represented in the front part). In the exemplary embodiment represented, three microswitches 42 are provided, which can be actuated by one, two or three permanent magnets 41. The number and position of the permanent magnets 41 therefore produces the encoding.

Figure 8:
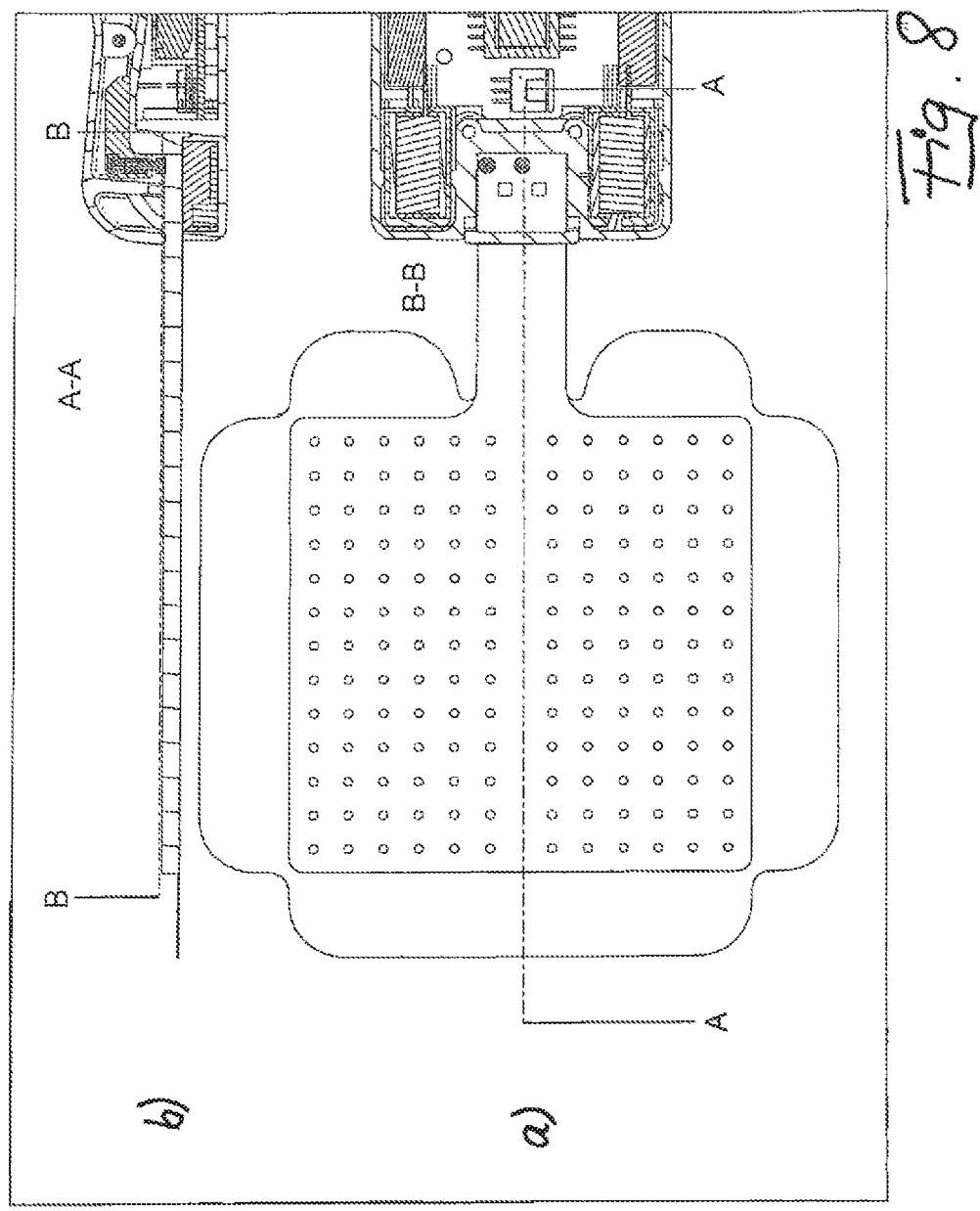
FIGS. 8a) and 8b) show the representations according to FIG. 7 in the connected state of the electrode unit and supply unit.

FIG. 8 shows the connected state of the electrode unit 1 and the supply unit 10. The vertical sectional representation of FIG. 9 illustrates the position, corresponding to the encoding according to FIG. 6, of the microswitches 42, two of which are attracted into a switching position by the permanent magnets 41, while one of the microswitches 42 remains in a spring-loaded inactive position because no permanent magnet 41 arranged for it in the appendage 6.

In the third exemplary embodiment, represented in a similar way in FIGS. 10 and 11, there is optical encoding 43 at the front end of the appendage 6 and a corresponding optical reading instrument 44 in the supply unit, having corresponding sensing positions which correspond to the positions of the optical encoding 43 when the electrode unit is inserted according to FIG. 11 into the supply unit 10. For example, the optical reading instrument 44 recognizes a blackened area as a "1" signal and an unblackened area as a "0" signal. Instead of this optical encoding, in one variant the appendage 6 may also be provided with a barcode and the supply unit 10 may comprise a barcode reader. The barcode itself may then contain information about the size of the treatment surface of the electrode instrument 1.

It is quite clear that any further optical or other encodings may be implemented in the scope of the present invention.

The invention claimed is:

1. A plasma treatment device for carrying out a dielectric barrier plasma discharge, comprising:
   at least one electrode unit comprising a treatment side;
   a supply unit with which the at least one electrode unit is mechanically connectable and is electrically contacted in order to be supplied with a supply voltage required for plasma generation,
   wherein the at least one electrode unit comprises an electrode arrangement shielded by a flat dielectric at least on the treatment side,
   wherein the supply unit is connectable to a plurality of different electrode units of different sizes each of which is configured to function as said at least one electrode unit, wherein said at least one electrode unit comprises an encoding which specifies a size and/or type of the at least one electrode unit;
   a recognition instrument which is part of or associated with the supply unit which recognizes the encoding of the at least one electrode unit when the at least one electrode unit is connected to the supply unit; and
   a control instrument which controls the supply unit to supply the at least one electrode unit with an amount of energy based on the size and/or type specified by the encoding of the at least one electrode unit.

2. The plasma treatment device as claimed in claim 1, wherein the at least one electrode unit comprises an appendage that is insertable into a recess of the supply unit, and wherein the appendage carries the encoding.

3. The plasma treatment device as claimed in claim 1 wherein the encoding is configured mechanically in the form of elevations, and wherein the recognition instrument is formed with rocker switches that are actuatable by the elevations.

4. The plasma treatment device as claimed in claim 3, wherein the rocker switches are configured for switching over the supply voltage in the supply unit.

5. The plasma treatment device as claimed in claim 1 wherein the encoding is configured in an optical form, and wherein the recognition instrument is an optical recognition instrument.

6. The plasma treatment device as claimed in claim 1 wherein the encoding utilizes at least one permanent magnet to actuate at least one switch of the supply unit.

7. The plasma treatment device as claimed in claim 1 wherein the at least one electrode unit is interrogatable by the recognition instrument.

8. The plasma treatment device as claimed in claim 7, further comprising a detector that is part of or associated with the supply unit which detects the connection established between the supply unit and the at least one electrode unit and thereupon generates an interrogation signal for the recognition instrument.

* * * * *